(12) United States Patent
Eller et al.

(10) Patent No.: US 9,301,735 B2
(45) Date of Patent: Apr. 5, 2016

(54) DRIVE SYSTEM FOR A BIOPSY MEMBER

(71) Applicant: Cook Medical Technologies LLC, Bloomington, IN (US)

(72) Inventors: Derek Roe Eller, Orient, OH (US); Ryan Nowicki, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 191 days.

(21) Appl. No.: 14/133,068

(22) Filed: Dec. 18, 2013

(65) Prior Publication Data
US 2014/0171825 A1   Jun. 19, 2014

Related U.S. Application Data

(60) Provisional application No. 61/739,317, filed on Dec. 19, 2012.

(51) Int. Cl.
*A61B 5/00* (2006.01)
*A61B 10/02* (2006.01)

(52) U.S. Cl.
CPC ..... *A61B 10/0233* (2013.01); *A61B 2010/0208* (2013.01)

(58) Field of Classification Search
CPC .. A61B 10/02; A61B 10/0233; A61B 10/025; A61B 10/0266; A61B 2010/0208; A61B 2010/0225
See application file for complete search history.

(56) References Cited

U.S. PATENT DOCUMENTS

| | | | |
|---|---|---|---|
| 1,257,532 A | 2/1918 | Risk | |
| 1,708,888 A | 4/1929 | Keeling | |
| 1,833,344 A | 11/1931 | West | |
| 2,381,112 A | 8/1945 | Clark | |
| 2,710,000 A | 6/1955 | Cromer et al. | |
| 2,850,007 A | 9/1958 | Lingley | |
| 3,683,891 A | 8/1972 | Eskridge et al. | |
| 5,018,530 A | 5/1991 | Rank et al. | |
| 5,133,713 A | 7/1992 | Huang et al. | |
| 5,221,269 A | 6/1993 | Miller et al. | |
| 5,488,958 A | 2/1996 | Topel et al. | |
| 6,027,458 A | 2/2000 | Janssens | |
| 6,083,237 A | 7/2000 | Huitema et al. | |
| 6,530,936 B1 | 3/2003 | Yun | |
| 6,620,111 B2 | 9/2003 | Stephens et al. | |
| 6,860,860 B2 | 3/2005 | Viola | |
| 7,008,381 B2 | 3/2006 | Janssens | |
| 7,419,472 B2 | 9/2008 | Hibner et al. | |
| 7,662,109 B2 | 2/2010 | Hibner | |
| 7,670,328 B2 | 3/2010 | Miller | |
| 7,850,620 B2 | 12/2010 | Miller et al. | |
| 7,867,173 B2 | 1/2011 | Hibner et al. | |
| 8,454,532 B2 * | 6/2013 | Hibner ............... | A61B 10/0275 600/562 |
| 8,951,208 B2 * | 2/2015 | Almazan ............ | A61B 10/0275 600/566 |
| 2002/0138021 A1 | 9/2002 | Pflueger | |
| 2007/0191732 A1 | 8/2007 | Voegele | |
| 2010/0317995 A1 | 12/2010 | Hibner et al. | |

* cited by examiner

*Primary Examiner* — Max Hindenburg
(74) *Attorney, Agent, or Firm* — Brinks Gilson & Lione

(57) ABSTRACT

A drive system is provided for rotating and translating a biopsy member. The drive system includes housing having an opening having housing threads. A device gear within the opening has device gear threads that mate with the housing threads. A biopsy member is fixed to the device gear. The device gear threads have gear teeth that mate with pinion teeth that are disposed circumferentially on a pinion. A drive is configured to rotate the pinion thereby rotating and translating the biopsy member relative to the housing.

20 Claims, 3 Drawing Sheets

DRIVE SYSTEM FOR A BIOPSY MEMBER

This application claims priority to U.S. Provisional Application No. 61/739,317, filed Dec. 19, 2012, which is hereby incorporated by reference herein.

BACKGROUND

The present invention relates generally to medical devices and more particularly to a biopsy member.

It is often necessary to obtain tissue samples for medical analysis and diagnosis. Physicians in many specialties commonly obtain biopsy samples in order to detect abnormalities, such as cancer.

Although there are numerous biopsy systems available, many biopsy systems use a member to cut a sample from inside a patient's body. Typically, the member may be a needle with a hollow longitudinal lumen and a sharp edge for cutting tissue. In order to retrieve the biopsy sample, the needle is inserted through the patient's skin, and the sharp edge cuts a tissue sample from inside the patient's body. The tissue sample is then collected inside of the longitudinal lumen of the needle. Alternatively, the biopsy member could be a brush or other collection instrument.

Various types of needles, cannulas, and other tissue collection structures may also be used in conjunction with a biopsy member. For example, a needle with a pointed tip may be inserted through the member, and may be used to guide the biopsy member to the desired target tissue. The member may also be inserted through a guide cannula or cutting cannula. The cannula may provide a pathway through non-targeted tissue to minimize damage to the non-targeted tissue. If the cannula has a sharp distal edge for cutting, the cannula may also be used to cut the tissue sample from the target tissue.

After the biopsy sample has been cut from the target tissue, the biopsy member may be withdrawn from the patient, and the biopsy sample may be retrieved from the distal end of the member. Alternatively, the biopsy sample may be retrieved from the longitudinal lumen of a biopsy needle while the needle remains in the patient's body by drawing the biopsy sample proximally through the lumen and out an exterior port of the biopsy needle.

One type of biopsy member that is used to collect biopsy samples has a helical screw blade at the distal end of a cannula. This type of biopsy member is typically driven into the target tissue by rotating the member so that the helical blade screws into the target tissue like a corkscrew. The tissue sample may then be separated from the target tissue by advancing a cutting cannula over the helical screw blade, or by withdrawing the member which causes the helical blade to longitudinally cut through portions of the sample that extend through the helical gap of the blade.

Biopsy members with helical screw blades are typically driven into the tissue by manually rotating the member. However, this has some disadvantages in practice. In particular, the length of time that a medical procedure takes increases the cost of the procedure and also can increase the anxiety of a patient. However, compared to some spring-loaded biopsy systems, manually driven helical screw members can be slower to use. Manually rotating a helical screw member can also be tedious for a physician, especially for a physician who performs numerous biopsies in hard tissue or bone. In addition, patients may be more psychologically affected by a manual biopsy system, when the patient is able to view the physician repeatedly moving his hand and/or wrist as the member is driven into their body. By comparison, a patient may be psychologically more comfortable with a biopsy system where the physician's body movements are minimized during the driving step of the procedure.

Accordingly, the inventor believes that an improved drive system for a biopsy member would be desirable for collecting biopsy samples.

SUMMARY

A drive system is provided for rotating and translating a biopsy member. The drive system includes a housing having an opening with threads. A device gear within the opening has device gear threads that mate with the housing threads. The biopsy member is fixed to the device gear. The device gear threads have gear teeth that mate with pinion teeth that are disposed circumferentially on a pinion. A drive is configured to rotate the pinion thereby rotating and translating the biopsy member relative to the housing. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
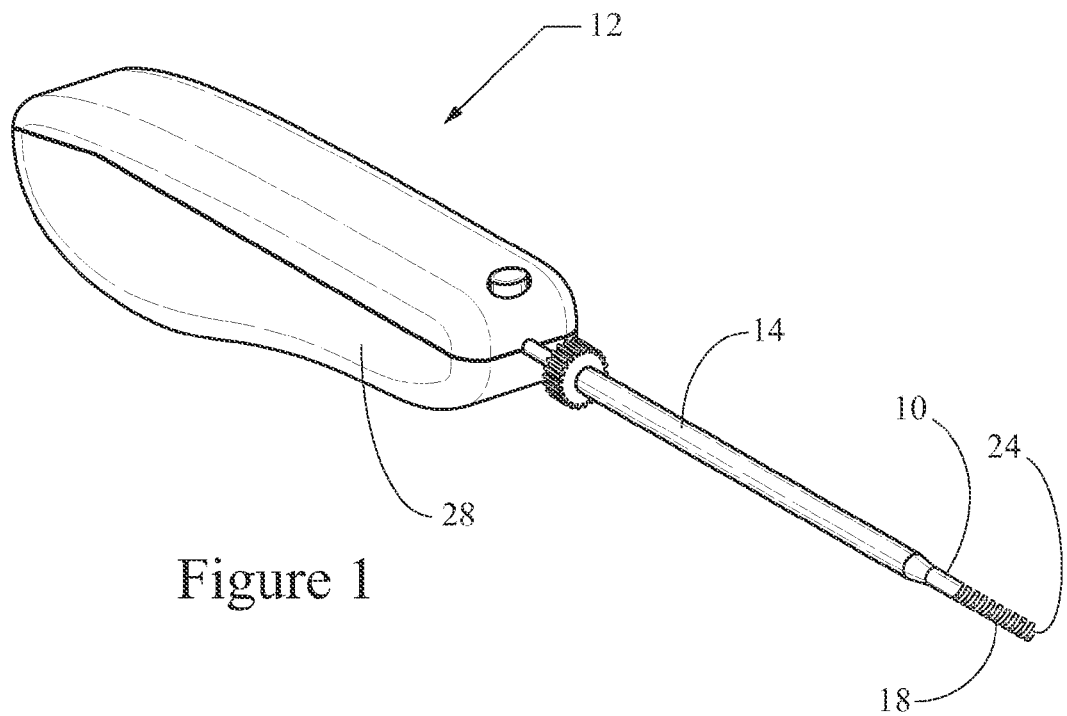
FIG. 1 is a perspective view of a biopsy system including a cutting cannula.
Figure 2:
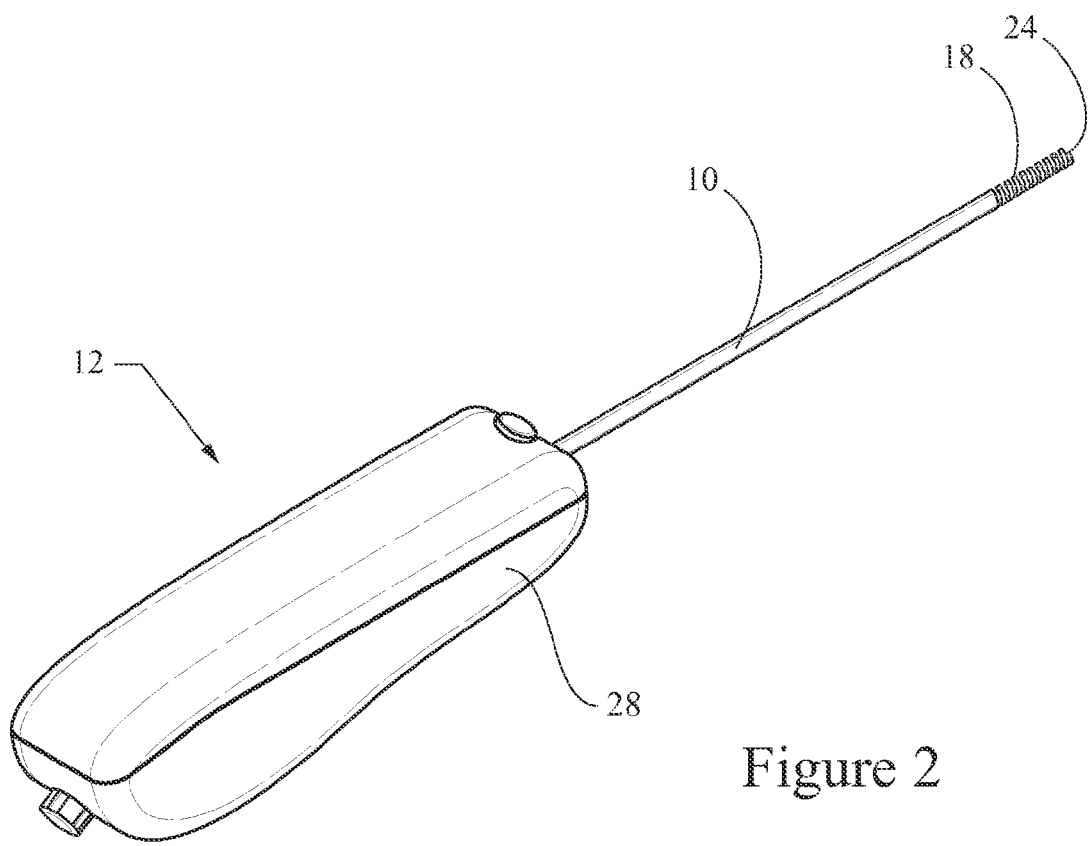
FIG. 2 is a perspective view of the biopsy system without a cutting cannula.
Figure 3:
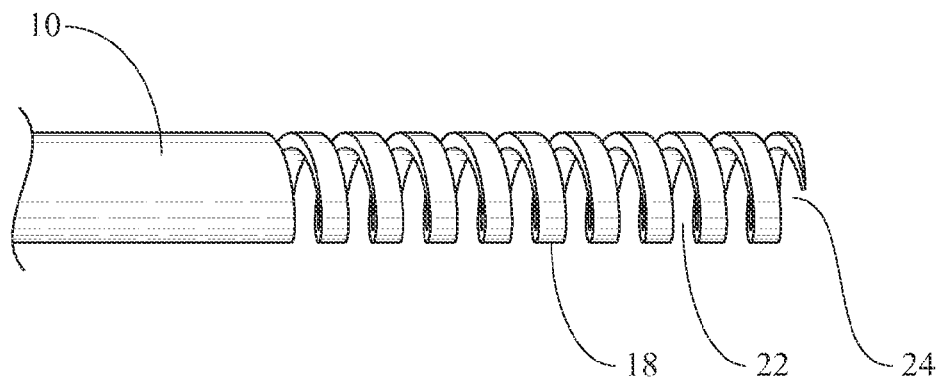
FIG. 3 is a close-up view of the distal end of the biopsy member.

Referring now to the figures, and particularly to FIGS. 1-3, a biopsy member 10 and a drive system 12 for the member 10 are shown. The biopsy member 10 may be inserted through a cutting cannula 14 to reach a target tissue. Typically, a needle such as a trocar needle with a pointed tip will be initially inserted through the cannula 14 so that the pointed tip is exposed at the distal end of the cannula 14. The needle and cannula 14 may then be driven into a patient's body by manually pushing the needle and cannula 14 together through the patient's tissues. Once the distal ends of the needle and cannula 14 are located close to the target tissue, the needle may be withdrawn from the cannula 14. The biopsy member 10 may then be inserted through the cannula 14 and may be longitudinally slid through the cannula 14 until the distal end of the member 10 reaches the distal end of the cannula 14.

The drive system 12 is then activated to rotationally and translationally drive the biopsy member 10 into the target tissue. The rotational and translational movement of the biopsy member 10 causes the hollow helical screw blade 18 at the distal end of the member 10 to screw into the target tissue. Once the desired tissue sample is positioned within the lumen of the member 10, the tissue sample can be separated from the target tissue by advancing the cannula 14 distally over the helical screw blade 18 or by withdrawing the member 10 into the cannula 14. In either case, the tissue sample within the lumen of the member 10 will initially be connected to the target tissue through the helical gap 22 of the screw blade 18 and at the distal opening 24 of the member 10. By advancing the cannula 14 over the screw blade 18, the sharp distal edge of the cannula 14 cuts through the connecting tissues extending through the helical gap 22 of the member 10. Alternatively, if the member 10 is withdrawn into the cannula 14, the proximal edge of the helical screw 18 cuts through the connecting tissues extending through the helical gap 22. In either event, the connected tissue at the distal opening 24 of the member 10 typically does not need to be separately cut loose from the target tissue, since this portion of the tissue will usually tear away when the biopsy member 10 is withdrawn. Thus, the tissue sample that is retrieved after the procedure is a complete cylindrical core disposed in the distal end of the lumen of the member 10.

As shown in FIGS. 1 and 2, a drive system 12 may be provided with the biopsy member 10 to provide rotational and translational movement of the biopsy member 10 relative to a housing 28. In particular, the drive system 12 can provide both rotational and translational movement of the biopsy member 10 simultaneously. Although the drive system 12 may be used with other types of biopsy members, the drive system 12 may be particularly useful with biopsy members 10 that have a hollow helical screw blade 18 at the distal end of the biopsy member 10. Thus, as shown in FIGS. 1 and 2, the biopsy member 10 extends longitudinally from the housing 28 of the drive system 12 and is rotatable and translatable relative to the housing 28. In addition, the housing 28 can be used as a handle for a user to hold the biopsy system.

Figure 4:
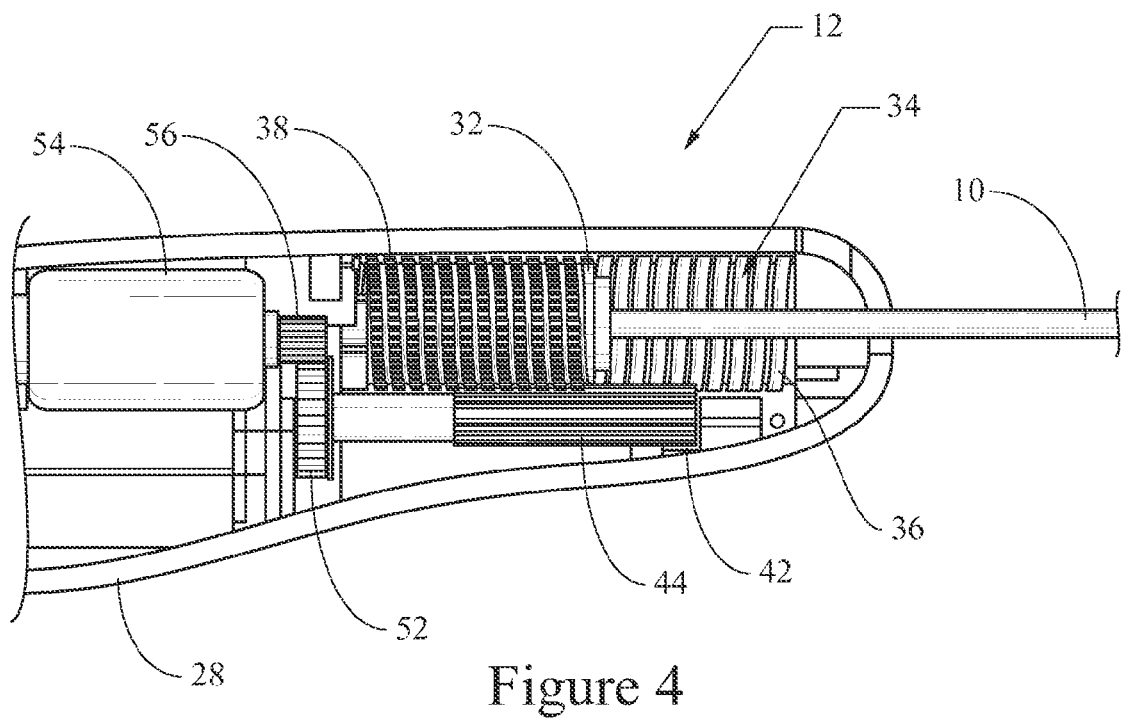
FIG. 4 is a side view of the internal drive system.
Figure 5:
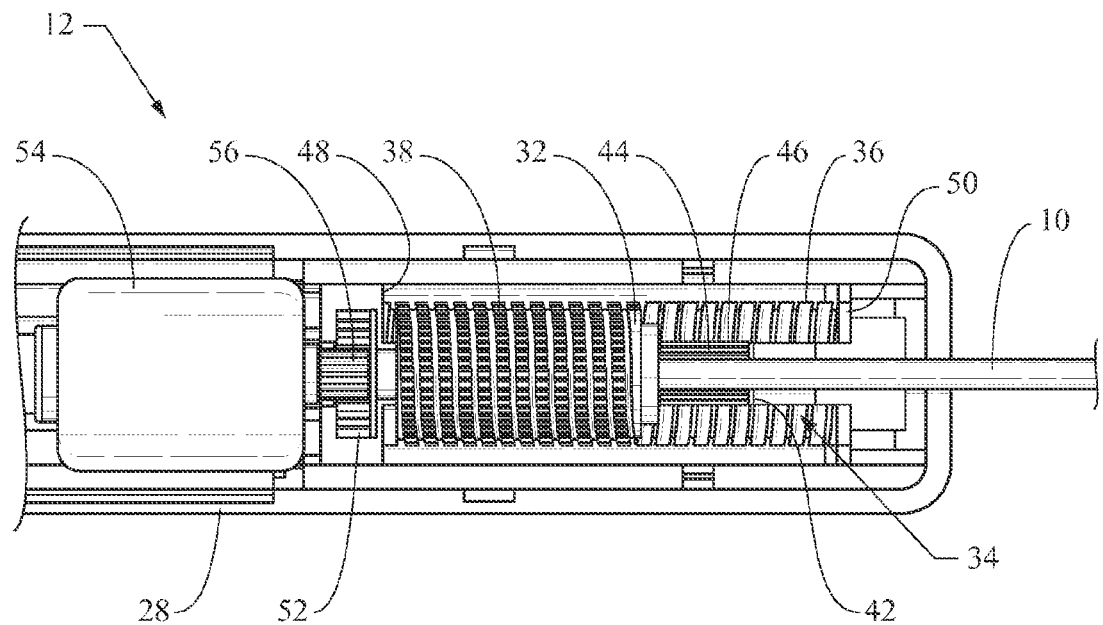
FIG. 5 is a top view of the internal drive system.
Figure 6:
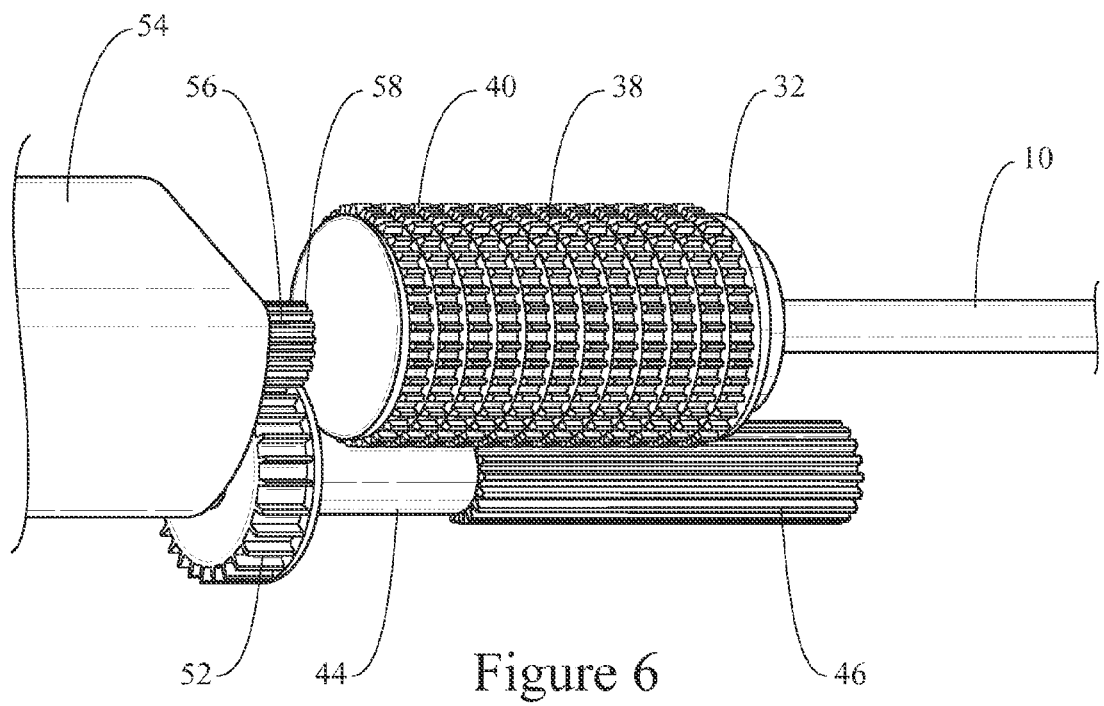
FIG. 6 is a perspective view of a portion of the internal drive system, showing the device gear, pinion, and motor.

As shown in FIGS. 4-6, the housing 28 has a device gear opening 34 having housing threads 36, and a device gear 32 is within the opening 34. The device gear 32 has device gear threads 38 that mate with the housing threads 36 such that the device gear 32 is rotatable and translatable relative to the housing 28. The opening 34 may also fix the rotational axis of the device gear 32 relative to the housing 28. For example, the opening 34 may restrict radial movement of the device gear 32 relative to the rotational axis. The biopsy member 10 can be fixed to the device gear 32 to allow the biopsy member 10 to also be rotatable and translatable relative to the housing 28. The biopsy member 10 can extend from the device gear 32 out an opening of the housing 28. Although components may be rotationally, translationally or otherwise fixed together herein by bonding separate components together, components that are fixed together and provide more than one function may also be made as integral components.

The device gear threads 38 include a series of device gear teeth 40. The device gear teeth 40 extend helically circumferentially around the device gear 32. As such, the device gear teeth 40 can form the device gear threads 38, and the device gear teeth 40 follow the path of the device gear threads 38. The helical path of the device gear teeth 40 can also follow the path of the grooves of the housing threads 36. The grooves of the housing threads 36 may be wide enough to accommodate the device gear teeth 40. The device gear teeth 40 are spaced from one another longitudinally along the length the device gear 32. The spaces between the device gear teeth 40 provide the grooves of the device gear threads 38 that accommodate the housing threads 36.

The housing 28 may also have a pinion opening 42 to accommodate a pinion 44. The pinion 44 can be connected to the housing 28 and be rotatable relative to the housing 28. The pinion 44 has a series of pinion teeth 46 disposed circumferentially thereon that mate with the device gear teeth 40. The pinion 44 may be substantially parallel to the device gear 32. For example, the pinion opening 42 can be substantially parallel to the device gear opening 34, and the device gear opening 34 and the pinion opening 42 can intersect thereby forming a slot so that the pinion teeth 46 can mate with the device gear teeth 40. When the pinion 44 is rotated, the device gear 32 rotates and translates within the device gear opening 34. The pinion 44 and/or the device gear 32 can be elongated in the direction of translational movement of the device gear 32 so that at least some of the device gear teeth 40 and the pinion teeth 46 remain mated as the device gear 32 translates relative to the pinion 44. For example, the pinion teeth 46 may be elongated along the direction of translational movement of the device gear 32, and the device gear teeth 40 can slide in the translational direction along the pinion teeth 46.

The device gear teeth 40 and pinion teeth 46 can have a variety of configurations to enable the device gear teeth 40 and pinion teeth 46 to mate and mesh in order to transmit rotational motion from the pinion 44 to the device gear 32. For example, the device gear teeth 40 can form rows of teeth. Each row can extend in the direction of translational movement and each row can be parallel to one another with the rows disposed circumferentially on the device gear 32. As described above, the device gear teeth 40 within a row are spaced from one another to accommodate the housing threads 36.

The housing 28 can further include a proximal stop 48 that is configured to prevent the device gear 32 from having translational movement beyond a proximal position. Similarly, the housing 28 can have distal stop 50 configured to prevent the device gear 32 from having translational movement beyond a distal position. The proximal stop 48 and the distal stop 50 can be, for example, a wall or other structure at the proximal and distal ends of the device gear opening 34 that restricts translational movement of the device gear 32 to that between the proximal and distal ends of the device gear opening 34. The translational movement of the device gear 32 can also be limited by other means such as by a switch that stops a drive 54 that translates the device gear 32 at the proximal and/or distal positions. For example, the switch may create a break in the circuit that provides electrical power to the drive 54.

The pinion teeth 46 may be disposed on a distal end of the pinion 44, and the pinion 44 may have a series of gearing teeth 52 disposed circumferentially on a proximal end of the pinion 44. The diameter of the distal end may be different from the diameter of the proximal end to adjust the rotational speed of the device gear 32 relative to the rotational speed of a drive 54. For example, the diameter of the proximal end may be larger than the diameter of the distal end of the pinion 44. Furthermore, the entire length of the pinion 44 may not have gearing teeth disposed circumferentially thereon. For example, the pinion 44 may have a region between the proximal end and the distal end that is devoid of teeth.

The drive system 12 can further include a drive 54 that is configured to rotate the pinion 44 which thereby rotates and translates the biopsy member 10 relative to the housing 28. The drive 54 may be fixed to the housing 28. The drive 54 can be a motor such as an electric motor as illustrated in FIGS. 4-6. However, the drive 54 may be a manual method of rotating the pinion 44 such as by twisting a component at a proximal end of the housing 12 which rotates the pinion 44. However, a motorized drive can be operated more easily by a user since less movement by the user may be required.

A drive gear 56 can be fixed to a drive shaft of the drive 54, and the drive gear 56 and drive shaft are rotatable relative to the housing 28. The drive gear 56 has a series of drive gear teeth 58 disposed circumferentially thereon. The drive gear teeth 58 mate with the gearing teeth 52 of the pinion 44 such that rotation of the drive gear 56 rotates the pinion 44. Alternatively, the drive shaft of the drive 54 may be fixed to the pinion 44. As such, the drive system 12 may not include the drive gear 56 and gearing teeth 52 of the pinion 44. Furthermore, the diameters of the gears such as the device gear 32, proximal and distal ends of the pinion 44, and the drive gear 56 may vary from those illustrated to select a desired rotational speed of the biopsy member 10. For example, the drive system 12 illustrated in FIGS. 4-6 has a ratio of rotational speed of the drive 54 to rotational speed of the drive gear 56 of about 20:1. However, other ratios can be selected based on rotational speed of the drive 54 and the desired rotational speed of the drive gear 56.

The rotational and translational movement of the device gear 32 can be configured so that the housing 28 is not moved relative to the target tissue. For example, if the biopsy member 10 includes a helical screw blade, the helical screw blade may cut helically or screw into the target tissue while the housing is not moved relative to the target tissue. By the helical screw blade moving both rotationally and translationally simultaneously, the helical screw blade may only cut helically resulting in substantially no pulling or pushing of the target tissue by the helical screw blade during advancement of the biopsy member 10 into the target tissue. For example, the device gear threads 38 may have substantially the same pitch as the pitch of the helical screw blade 18. By not having to move the housing, the rotational and translational movement of the biopsy member 10 into the target tissue can be more precisely controlled. For example, the distances the biopsy member 10 is inserted into the target issue can controlled by the distal stop 50 of the housing 28.

When an electric motor is used for the drive 54, the electric motor can be powered by a battery in the housing 28 or by an external power source electrically connected to the electric motor. The electric motor can be activated by a switch or other controls on the housing 28. The drive system 12 may be further configured to be able to have the biopsy member 10 reverse or retract toward the housing 28. For example, the electric motor can reverse rotation compared to motor rotation during advancement of the biopsy member 10. The housing 28 may have a second switch or other controls that retracts the biopsy member 10. Being able to retract the biopsy member 10 can allow for multiple insertions into target tissue so that multiple samples can be retrieved.

The drive system 12 can also be relatively compact so that the biopsy system can be more easily operated. For example, the drive shaft and/or the drive gear 56 can be positioned longitudinally relative to the device gear 32 and within a circumference of the device gear 32. By having the drive shaft generally along the rotational axis of the device gear 32, the circumference of the housing around the drive system 12 can be minimized. Moreover, the drive system 12 can be light enough to be left freely-standing in a patient without causing discomfort. The biopsy member 10 may also be configured to be disconnected from the drive system 12. For example, the biopsy member 10 may be removably fixed to the device gear 32.

As previously described, the biopsy member 10 may have a lumen where the target tissue can be pulled into. Suction can be pulled through the lumen of the biopsy member 12 in order to pull the target tissue into the lumen. In order to provide suction to the lumen, the housing 28 may have an external aspiration port, and the external aspiration port can be in fluid communication with the lumen.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A drive system to rotate and translate a biopsy member having a proximal part extending to a distal part, the drive system comprising:
   a housing comprising a device gear spacing and having housing threads;
   a device gear within the device gear spacing of the housing, the device gear having device gear threads that mate with the housing threads such that the device gear is rotatable and translatable relative to the housing, the device gear being fixed to the proximal part of the biopsy member, the device gear threads comprising a series of device gear teeth;
   a pinion comprising a series of pinion teeth disposed circumferentially thereon that mate with the device gear teeth, the pinion being connected to and disposed within the housing, the pinion being rotatable relative to the housing; and
   a drive operable to rotate the pinion, the biopsy member extending from the proximal part and out of the housing to the distal part wherein rotating the pinion rotates and translates the device gear and the biopsy member relative to the housing.

2. The drive system according to claim 1, wherein the pinion teeth are disposed on a distal end of the pinion, and the pinion further comprises a proximal end having a diameter larger than a diameter of the distal end, the proximal end having a series of gearing teeth disposed circumferentially thereon.

3. The drive system according to claim 2, further comprising a drive gear fixed to a drive shaft of the drive, the drive gear comprising a series of drive gear teeth to mate with the gearing teeth of the pinion.

4. The drive system according to claim 3, wherein a diameter of the drive gear is smaller than the diameter of the proximal end of the pinion.

5. The drive system according to claim 3, wherein the drive shaft of the drive is substantially parallel to a rotational axis of the device gear.

6. The drive system according to claim 3, wherein the drive shaft being positioned longitudinally relative to the device gear and within a circumference of the device gear.

7. The drive system according to claim 1, wherein the drive comprises an electric motor.

8. The drive system according to claim 1, wherein the housing comprises a proximal stop configured to prevent the device gear from having translational movement beyond a proximal position and a distal stop configured to prevent the device gear from having translational movement beyond a distal position.

9. The drive system according to claim 1, wherein the device gear and the pinion are elongated along a direction parallel to translational movement of the device gear.

10. The drive system according to claim 9, wherein the housing comprises a pinion spacing parallel to the device gear spacing, the pinion being within the pinion spacing, the device gear spacing and the pinion spacing intersect thereby forming a slot so that the pinion teeth can mate with the device gear teeth.

11. A drive system to rotate and translate a biopsy member to target tissue, the drive system comprising:

the biopsy member having a proximal part extending to a distal part, the distal part of the biopsy member comprises a hollow helical screw blade;

a housing comprising a device gear spacing and having housing threads;

a device gear within the device gear spacing of the housing, the device gear having device gear threads that mate with the housing threads such that the device gear is rotatable and translatable relative to the housing, the device gear being fixed to the proximal part of the biopsy member, the device gear threads comprising a series of device gear teeth;

a pinion comprising a series of pinion teeth disposed circumferentially thereon that mate with the device gear teeth, the pinion being connected to and disposed within the housing, the pinion being rotatable relative to the housing; and a drive operable to rotate the pinion, the biopsy member extending from the proximal part and out of the housing to the distal part wherein rotating the pinion rotates and translates the device gear and the biopsy member relative to the housing.

12. The drive system according to claim 11, wherein the device gear threads have a pitch that is substantially the same as a pitch of the helical screw blade.

13. The drive system according to claim 11, wherein the helical screw blade is operable to helically screw into target tissue while the housing is not moved relative to target tissue.

14. The drive system according to claim 1, wherein a diameter of the device gear being larger than a diameter of the pinion.

15. The drive system according to claim 1, wherein a diameter of the device gear being larger than a diameter of the biopsy member.

16. The drive system according to claim 1, wherein a rotational axis of the device gear is fixed relative to the housing.

17. The drive system according to claim 1, wherein the device gear teeth comprise a series of rows of teeth with each row extending along a direction of translational movement of the device gear.

18. The drive system according to claim 17, wherein the teeth within each row of teeth are spaced from one other to accommodate the housing threads.

19. The drive system according to claim 1, wherein the pinion is elongated along a direction parallel to translational movement of the device gear, the pinion teeth are disposed on a distal end of the pinion, and the pinion further comprises a proximal end having a diameter larger than a diameter of the distal end, the proximal end having a series of gearing teeth disposed circumferentially thereon.

20. The drive system according to claim 19, wherein a diameter of the device gear being larger than the diameter of the distal end of the pinion.

* * * * *